United States Patent
Lowery et al.

(10) Patent No.: US 11,788,873 B2
(45) Date of Patent: Oct. 17, 2023

(54) SYSTEMS, METHODS AND APPARATUSES PROVIDING NOISE REMOVAL FOR FLOW SENSING COMPONENTS

(71) Applicant: Honeywell International Inc., Charlotte, NC (US)

(72) Inventors: Steven Daniel Lowery, Charlotte, NC (US); Gautham Kashim Adapparaju, Bangalore (IN); Vikram Bhat, Bangalore (IN)

(73) Assignee: Honeywell International Inc., Charlotte, NC (US)

( * ) Notice: Subject to any disclaimer, the term of this patent is extended or adjusted under 35 U.S.C. 154(b) by 59 days.

(21) Appl. No.: 17/588,480

(22) Filed: Jan. 31, 2022

(65) Prior Publication Data

US 2023/0194318 A1    Jun. 22, 2023

(30) Foreign Application Priority Data

Dec. 17, 2021  (IN) .............................. 202111058918

(51) Int. Cl.
| | |
|---|---|
| *G01F 1/84* | (2006.01) |
| *G01F 1/40* | (2006.01) |
| *G01F 1/684* | (2006.01) |
| *A61B 5/00* | (2006.01) |

(52) U.S. Cl.
CPC .............. *G01F 1/40* (2013.01); *G01F 1/6842* (2013.01); *G01F 1/8436* (2013.01); *A61B 5/7203* (2013.01)

(58) Field of Classification Search
CPC ........ G01F 1/40; G01F 1/6842; G01F 1/8436; A61B 5/7203
See application file for complete search history.

(56) References Cited

U.S. PATENT DOCUMENTS

| | | | |
|---|---|---|---|
| 5,504,692 A | 4/1996 | Cardner | |
| 2006/0174628 A1* | 8/2006 | Mikhail | ................. B64D 13/00 60/785 |
| 2006/0277992 A1* | 12/2006 | Calabrese | ............. G01F 23/266 73/304 R |

(Continued)

FOREIGN PATENT DOCUMENTS

| | | | |
|---|---|---|---|
| CN | 100545588 C | 9/2009 | |
| EP | 2154529 B1 * | 12/2013 | ......... G01N 33/0063 |

(Continued)

OTHER PUBLICATIONS

European search report dated May 2, 2023 for EP Application No. 22207196, 9 page(s).

*Primary Examiner* — Ryan D Walsh
(74) *Attorney, Agent, or Firm* — Alston & Bird LLP

(57) ABSTRACT

Methods, apparatuses and systems for providing dehumidification providing dehumidification for gas detecting components are disclosed herein. An example apparatus may comprise: a flow sensing component configured to detect a flow rate associated with a flowing media in a flow channel of the apparatus; and a controller component in electronic communication with the flow sensing component that is configured to receive a flow rate indication from the flow sensing component, and in response to determining that the flow rate indication satisfies a null condition threshold, apply an exponential smoothing function with a variable alpha value to condition an output signal of the apparatus.

20 Claims, 7 Drawing Sheets

(56) References Cited

U.S. PATENT DOCUMENTS

| | | | |
|---|---|---|---|
| 2009/0064796 A1 | 3/2009 | Mehendale et al. | |
| 2015/0320357 A1 | 11/2015 | Kuraguntla et al. | |
| 2018/0166060 A1* | 6/2018 | Grubb | F04C 14/28 |
| 2018/0231989 A1 | 8/2018 | Grubb | |
| 2018/0259360 A1* | 9/2018 | Mullis | G01L 19/12 |
| 2020/0319127 A1* | 10/2020 | Sorenson | G01N 27/123 |
| 2022/0283007 A1* | 9/2022 | Speldrich | G01F 1/696 |
| 2022/0390268 A1* | 12/2022 | den Haan | G01F 25/0092 |

FOREIGN PATENT DOCUMENTS

| | | | |
|---|---|---|---|
| GB | 1541419 A | 2/1997 | |
| JP | 11-101672 A | 4/1999 | |
| WO | WO-2015126703 A1 * | 8/2015 | A61B 5/026 |

* cited by examiner

SYSTEMS, METHODS AND APPARATUSES PROVIDING NOISE REMOVAL FOR FLOW SENSING COMPONENTS

CROSS-REFERENCE TO RELATED APPLICATIONS

This application claims priority to Indian Application No. 202111058918, filed Dec. 17, 2021, the contents of which are hereby incorporated herein in its entirety by reference.

BACKGROUND

Flow sensors may be used to measure a flow rate and/or quantity of a flowing media or gaseous substance and may be implemented in various applications. Such flow sensors are plagued by technical challenges and limitations. Through applied effort, ingenuity, and innovation, many of these identified problems have been solved by developing solutions that are included in embodiments of the present disclosure, many examples of which are described in detail herein.

BRIEF SUMMARY

Various embodiments described herein relate to methods, apparatuses, and systems for turbulent flow noise removal for an apparatus such as, for example, a flow sensing apparatus.

In accordance with various examples of the present disclosure, an apparatus is provided. The apparatus may comprise: a flow sensing component configured to detect a flow rate associated with a flowing media in a flow channel of the apparatus; and a controller component in electronic communication with the flow sensing component that is configured to receive a flow rate indication from the flow sensing component, and in response to determining that the flow rate indication satisfies a null condition threshold, apply an exponential smoothing function with a variable alpha value to condition an output signal of the apparatus.

In some examples, the controller component is further configured to, subsequent to applying the exponential smoothing function, perform compensation operations.

In some examples, the null condition threshold is between −25 and +25 standard cubic centimeter per minute (SCCM).

In some examples, the apparatus comprises a mass flow sensor or a liquid flow sensor.

In some examples, the exponential smoothing function is applied to a digital front-end of the apparatus.

In some examples, the controller component comprises an application-specific integrated circuit (ASIC).

In some examples, a value of alpha is 1 outside the null condition threshold, and wherein the value of alpha is 0.3 at a null condition.

In accordance with various examples of the present disclosure, a method is provided. The method may comprise receiving, by a controller component, a flow rate indication from a flow sensing component that is configured to detect a flow rate of a flowing media in a flow channel of the apparatus; and in response to determining, by the controller component, that the flow rate indication satisfies a null condition threshold, applying an exponential smoothing function with a variable alpha value to condition the output signal.

In accordance with various examples of the present disclosure, a computer program product for filtering noise from an output signal of an apparatus is provided. The computer program product may comprise at least one non-transitory computer-readable storage medium having computer executable program code instructions therein, the computer executable program code instructions comprising program code instructions configured, upon execution, to: receive, from a flow sensing component, a flow rate indication associated with a flowing media in a flow channel of the apparatus; and in response to determining that the flow rate indication satisfies a null condition threshold, apply an exponential smoothing function with a variable alpha value to condition the output signal.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
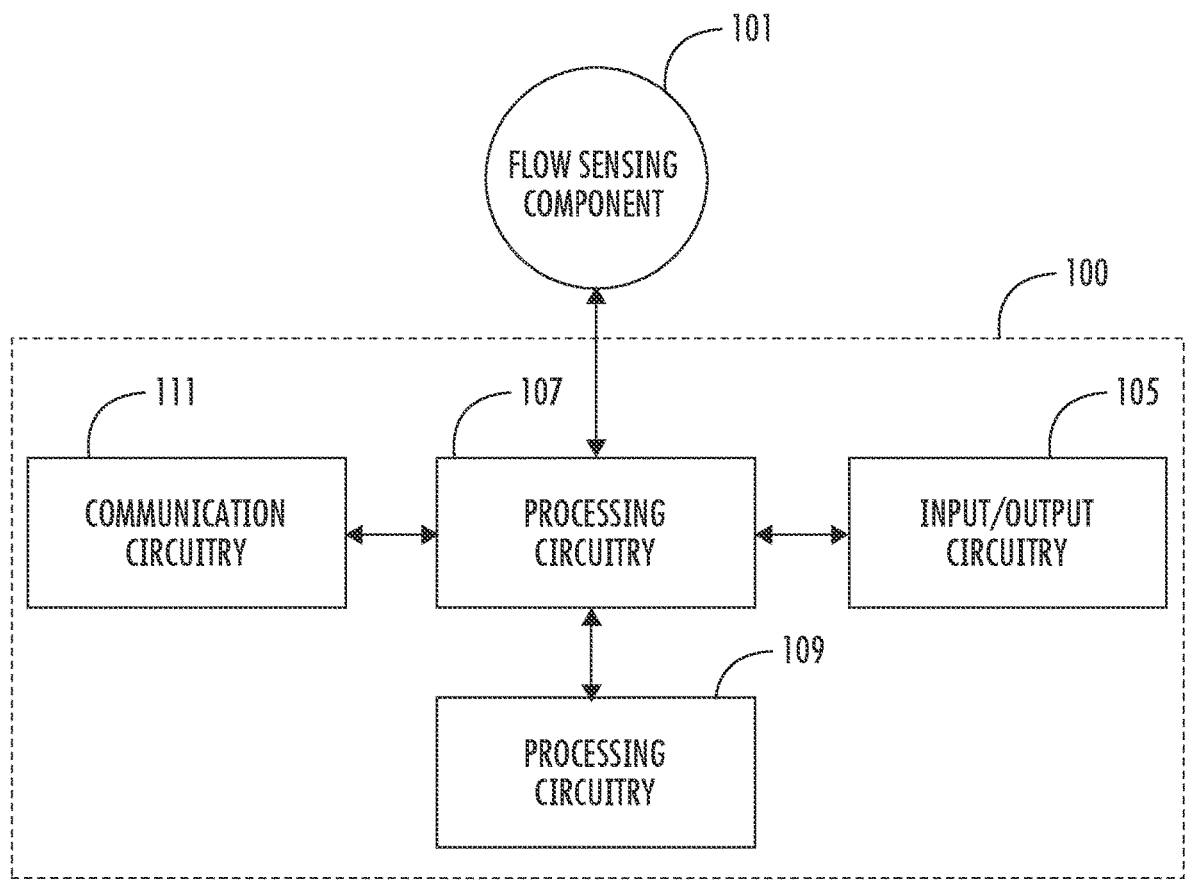
FIG. 1 illustrates a schematic diagram depicting an example apparatus in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such components or features may be optionally included in some embodiments, or may be excluded.

The term "electronically coupled" or "in electronic communication with" in the present disclosure refer to two or more electrical elements (for example, but not limited to, an example processing circuitry, communication module, input/output module memory, humidity sensing component, cooling element, gas detection component) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

The term "flow sensing device" refers to an apparatus that may detect, measure, and/or identify flow rate(s) (including, but not limited to, linear flow velocity, nonlinear flow velocity, mass flow rate, and/or volumetric flow rate) of a flowing media or medium. In the present disclosure, the term "flowing media" refers to a substance (such as, but not limited to, a liquid substance and/or a gaseous substance).

The term "flow path" may refer to a passageway through which a flowing media may flow, traverse or be conveyed. An example flow path of the present disclosure may be defined/formed by and/or comprise a plurality of channels. In various examples of the present disclosure, example dimensions of example cross sections of example flow channels may be in the microns to hundreds of microns in height and tens of microns to hundreds of microns in width. In various examples of the present disclosure, example flow channels may be greater than one hundred microns in length.

The term "laminar flow" may may be characterized by particles of a flowing media following smooth path(s) in the flow channel with little or no mixing (i.e., high momentum diffusion and low momentum convection). In contrast, the term "turbulent flow" may be characterized by particles of the flowing media undergoing irregular fluctuations, or mixing.

The term "thermal conductivity" may refer to a measure of the ability of a substance (for example, a gaseous substance such as air) to transfer energy (in the form of heat). Typically, a substance having a low thermal conductivity transfers heat at a lower rate than a substance having a high thermal conductivity. Measurements of thermal conductivity are necessary for a variety of sensor-based apparatuses and methods. The transfer of heat may be in the form of "thermal conduction," which may be defined as energy transfer due to microscopic particle collisions and/or electron movements across a temperature gradient. The energy that is transferred by a substance due to thermal conduction may also be referred to as the "heat conduction" of the substance for the purpose of calculating a thermal conductivity. The heat conduction may be quantified by the following vector:

$$q(r,t)$$

where r indicates the position associated with the heat conduction, and t indicates the time associated with the heat conduction. Because heat flows from a high temperature location to a low temperature location, the law of heat conduction (also known as Fourier's Law) provides that the heat transfer rate through a substance is proportional to the negative temperature gradient. The Fourier's Law may be provided in the following tensorial form:

$$q(r,t) = -\kappa \cdot \nabla T(r,t)$$

where q(r,t) is the heat conduction, and $\nabla T(r, t)$ is the temperature gradient tensor. $\kappa$ is the second-tensor of thermal conductivity (also known as the "thermal conductivity tensor"), which may correlate to the thermal conductivity of the substance. Based on the above tensorial form of Fourier's Law, the thermal conductivity tensor may be calculated based on:

$$\kappa = -\frac{q(r, t)}{\nabla T(r, t)}$$

As shown in the equation above, the thermal conductivity tensor $\kappa$ may be affected by the temperature gradient tensor $\nabla T(r, t)$. In other words, the thermal conductivity of a gaseous substance may be affected by its temperature. The General Gas Equation (also known as the Ideal Gas Law) provides that the temperature of the gaseous substance may be affected by its pressure:

$$PV = nRT = Nk_BT$$

where P is the pressure of the gaseous substance, T is the temperature of the gaseous substance, V is the volume of the gaseous substance, n is the amount of the gaseous substance, N is the number of gas molecules, R is the gas constant, and $k_B$ is the Boltzmann constant.

In some embodiments of the present disclosure, example methods, apparatuses, and systems may provide an apparatus for calculating, for example but not limited to, a thermal conductivity of a gaseous substance (such as air) based on, for example but not limited to, the Fourier's Law and the General Gas Equation described above.

Flow sensing devices may be utilized in a variety of applications including medical and industrial application. For example, flow sensing devices may be utilized in micropipetting, high-performance liquid chromatography (HPLC) applications, drug delivery, respirators, ventilators, Anesthesia machines, heating, ventilation, and air conditioning (HVAC) equipment, gas analyzers, leak detection equipment, and/or the like. For example, a flow sensing device may be implemented in a drug delivery system to detect, measure, and/or identify a flow rate of a flowing media associated therewith. In another example, a flow sensing device may be implemented in an automotive application in order to determine an amount of air flow entering an engine.

Referring now to FIG. 1, an example schematic diagram depicting an example controller component 100 of an example apparatus in accordance with various embodiments of the present disclosure is provided. In particular, the example controller component 100 includes input/output circuitry 105, processing circuitry 107, memory circuitry 109, and communications circuitry 111. Additionally, the controller component 100 is electrically coupled to and/or in electronic communication with a flow sensing component 101. The flow sensing component 101, input/output circuitry 105, the processing circuitry 107, the memory circuitry 109, and the communications circuitry 111 may be electronically coupled so that they may transmit and/or exchange information and data via wired or wireless connections between and among one another.

The flow sensing component 101 may be or comprise at least one sensing element (e.g., flow sensing element). As used herein, the term "sensing element" refers to an apparatus/device that measures or detects a property associated with the location or environment surrounding the sensing element, and may further indicate, record, and/or output the record of the property. For example, the flow sensing component 101 may be or comprise a transducer, for detecting and/or measuring an air flow rate that may be caused by, for example, the heat transfer. In some embodiments, the flow sensing component 101 may comprise a micro-electromechanical system (MEMS) flow sensing die. The MEMS flow sensing die may include miniaturized mechanical and electro-mechanical components for detecting and/or measuring air flow, and these components may be fabricated (such as through a microfabrication process) to form a functional circuit on a block of semiconducting material (such as a die). In some embodiments, the flow sensing component 101 may comprise a heater resistor and at least one temperature-sensing resistor that are disposed on a substrate. In some embodiments, the heater resistor may maintain a constant temperature (for example but not limited to, 150° C.). The heater resistor may be disposed between two temperature-sensing resistors.

In some embodiments, the flow sensing element of the flow sensing component 101 may be positioned on a flow path of a gaseous substance. For example, the two temperature-sensing resistors may be configured such that one of the resistors is located upstream and the other resistor is located downstream. In such embodiments, the gaseous substance moves from the upstream temperature-sensing resistor to the downstream temperature-sensing resistor, passing the heater resistor. The gaseous substance may reduce the temperature detected by the upstream temperature-sensing resistor, and increase the temperature detected by the downstream temperature-sensing resistor. As such, flow sensing component 101 may detect the air flow and/or calculate the air flow rate based on a heat transfer rate associated with the temperature-sensing resistors.

Referring back to FIG. 1, the flow sensing component 101 may be electronically coupled to the processing circuitry 107, and may provide one or more inputs to the processing circuitry 107. For example, the flow sensing component 101 may be configured to transmit a first signal indicative of an air flow rate (or flow rate of another gaseous substance such as a liquid) detected by the flow sensing component 101.

As used herein, the term "processing circuitry" refers to a circuitry or circuitries that may be configured to perform processing functions and/or software instructions on one or more input signals to generate one or more output signals. In various embodiments of the present disclosure, the processing circuitry 107 may perform processing functions and/or software instructions on signals that are received from the flow sensing component 101 to calculate the thermal conductivity of the gaseous substance based on, for example but not limited to, the Fourier's Law and the General Gas Equation described above.

In some embodiments, the processing circuitry 107 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 107 may comprise one or more processors. In one exemplary embodiment, the processing circuitry 107 is configured to execute instructions stored in the memory circuitry 109 or otherwise accessible by the processing circuitry 107. When executed by the processing circuitry 107, these instructions may enable the controller component 100 to execute one or a plurality of the functions as described herein. No matter whether it is configured by hardware, firmware/software methods, or a combination thereof, the processing circuitry 107 may comprise entities capable of executing operations according to the embodiments of the present invention when correspondingly configured. Therefore, for example, when the processing circuitry 107 is implemented as an ASIC, an FPGA, or the like, the processing circuitry 107 may comprise specially configured hardware for implementing one or a plurality of operations described herein. In these examples, the ASIC is an integrated circuit that may be customized for processing signals. In some examples, the ASIC may be fully customized or semi-customized for the particular application of processing signals. In some examples, the ASIC may be a programmable ASIC that allows circuit reconfiguration. In some embodiments, other suitable forms of the processing circuitry 107 may be implemented. Alternatively, as another example, when the processing circuitry 107 is implemented as an actuator of instructions (such as those that may be stored in the memory circuitry 109), the instructions may specifically configure the processing circuitry 107 to execute one or a plurality of algorithms and steps/operations described herein, such as those discussed with reference to FIG. 7. Referring back to FIG. 1, the processing circuitry 107 may be electronically coupled to the input/output circuitry 105, memory circuitry 109 and/or the communications circuitry 111.

As depicted in FIG. 1, in some embodiments, the controller component 100 may comprise memory circuitry 109. The memory circuitry 109 may be non-transitory and may include, for example, one or more volatile and/or non-volatile memories. The memory circuitry 109 may be configured to store information and data (such as processing functions and/or software instructions). The memory circuitry 109, together with the processing circuitry 107, may cause the controller component 100 to perform various processing functions and/or software instructions in accordance with example embodiments of the present disclosure, including, for example, calculating the thermal conductivity of the gaseous substance. In some embodiments, the memory circuitry 109 may comprise, for example, a volatile memory, a non-volatile memory, or a certain combination thereof. Although illustrated as a single memory in FIG. 1, the memory circuitry 109 may comprise a plurality of memory components. In various embodiments, the memory circuitry 109 may comprise, for example, a hard disk drive, a random access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory circuitry 109 may be configured to store information, data, application programs, instructions, and etc., so that the controller component 100 can execute various functions according to the embodiments of the present disclosure. For example, in at least some embodiments, the memory circuitry 109 is configured to cache input data for processing by the processing circuitry 107. Additionally or alternatively, in at least some embodiments, the memory circuitry 109 is configured to store program instructions for execution by the processing circuitry 107. The memory circuitry 109 may store information in the form of static and/or dynamic information. When the functions are executed, the stored information may be stored and/or used by the controller component 100.

As depicted in FIG. 1, in some embodiments, the controller component 100 may comprise communications circuitry 111. The communications circuitry 111 may comprise, for example, a device or circuitry embodied in either hardware or a combination of hardware and software that is configured to receive and/or transmit data from/to a network and/or any other device, circuitry, or module in communication with the controller component 100 and/or the flow sensing component 101. In this regard, the communications circuitry 111 may include, for example, a network interface for enabling communications with a wired or wireless communication network. In some embodiments, the communications circuitry 111 may be implemented as any apparatus included in a circuit, hardware, a computer program product or a combination thereof, which is configured to receive and/or transmit data from/to another component or apparatus. The computer program product comprises computer-readable program instructions stored on a computer-readable medium (for example, the memory circuitry 109) and executed by a controller component 100 (for example, the processing circuitry 107). In some embodiments, the communications circuitry 111 (as with other components discussed herein) may be at least partially implemented as the processing circuitry 107 or otherwise controlled by the processing circuitry 107. In this regard, the communications circuitry 111 may communicate with the processing circuitry 107, for example, through a bus. The communications circuitry 111 may comprise, for example, antennas, transmitters, receivers, transceivers, network interface cards and/or supporting hardware and/or firmware/software, and is used for establishing communication with another apparatus. The communications circuitry 111 may be configured to receive and/or transmit any data that may be stored by the memory circuitry 109 by using any protocol that can be used for communication between apparatuses. The communications circuitry 111 may additionally or alternatively communicate with the input/output circuitry 105, memory circuitry 109, and/or any other component of the controller component 100, for example, through a bus.

In some embodiments, the controller component 100 may comprise an input/output circuitry 105. The input/output circuitry 105 may communicate with the processing circuitry 107 to receive instructions input by the user and/or to provide audible, visual, mechanical or other outputs to the user. Therefore, the input/output circuitry 105 may comprise supporting devices, such as a keyboard, a mouse, a display, a touch screen display, and/or other input/output mechanisms. Alternatively, at least some aspects of the input/output circuitry 105 may be implemented on a device used by the user to communicate with the controller component 100. The input/output circuitry 105 may communicate with the memory circuitry 109, the communications circuitry 111 and/or any other component, for example, through a bus. One or a plurality of input/output circuitries and/or other components may be included in the controller component 100.

In various examples, the flow sensing component 101 may generate a flow rate indication and transmit the flow rate indication to the processing circuitry 107. Accordingly, the flow sensing component 101 and the controller component 100 may operate to generate measurements indicating a flow rate associated with a flowing media in a flow channel/path of an apparatus (e.g., flow sensing device).

In FIG. 1, although components 101, 105, 107, 109, and 111 may be described with respect to functional limitations, it is contemplated that the particular implementations necessarily include the use of particular hardware. It is also contemplated that certain of these components 101, 105, 107, 109, and 111 may additionally include one or more similar or common hardware. For example, the flow sensing component 101 may additionally include a processing circuitry, such that the flow sensing component 101 may process the signals generated by a flow sensing element to calculate the thermal conductivity. In various examples, the controller component 100 may operate to generate and provide measurements indicating a flow rate of a flowing media within the example apparatus (e.g., flow sensing device).

While the description above provides an example controller component 100, it is noted that the scope of the present disclosure is not limited to the description above. In some examples, an example controller component may may comprise one or more additional and/or alternative elements, and/or may be structured/positioned differently than that illustrated in FIG. 1.

As described above, many flow sensing devices are plagued by technical challenges and limitations. As noted above, laminar flow may be characterized by particles of a flowing media following smooth path(s) in a flow channel with little or no mixing while turbulent flow may be characterized by particles of a flowing media undergoing irregular fluctuations, or mixing. In some examples, a laminar flow for a flow sensing device may be achieved based on the flow rate of the flowing media. For example, flow sensing devices (e.g., mass flow sensors) may include flow tubes intended to laminarize flow in order to attain an accurate flow measurement. Similarly, fluid flow sensors may comprise specially designed flow tubes which operate to reduce turbulence of a flowing media/fluid as it passes through a sense element. Said differently, ideally a flow of a flowing media (e.g., air) should be laminar as it passes over a sensing element. In various examples, turbulent flow of a flowing media within an example flow sensing device may induce a noisy signal which may affect the accuracy of measurements generated by the flow sensing device.

In some examples, even in an instance of laminar flow, there may be unwanted fluctuations in an output signal related to externally-induced influences, or noise in a flow signal being measured/detected by a flow sensing component (e.g., flow transducer) such as vibrational and/or or pressure fluctuations that the example flow sensing device may be subject to. These externally-induced influences may cause an observable dithering of the output signal. In a digital flow sensor, the flow transducer signal is digitally quantized as a number represented in counts. The noise, which as noted above is in fact an unwanted signal caused by external influences such as vibrations or pressure fluctuations, can be observed as a peak-to-peak number of counts in the measured data where the magnitude of noise is dependent on the flow rate of a flowing media (e.g., air).

Figure 2:
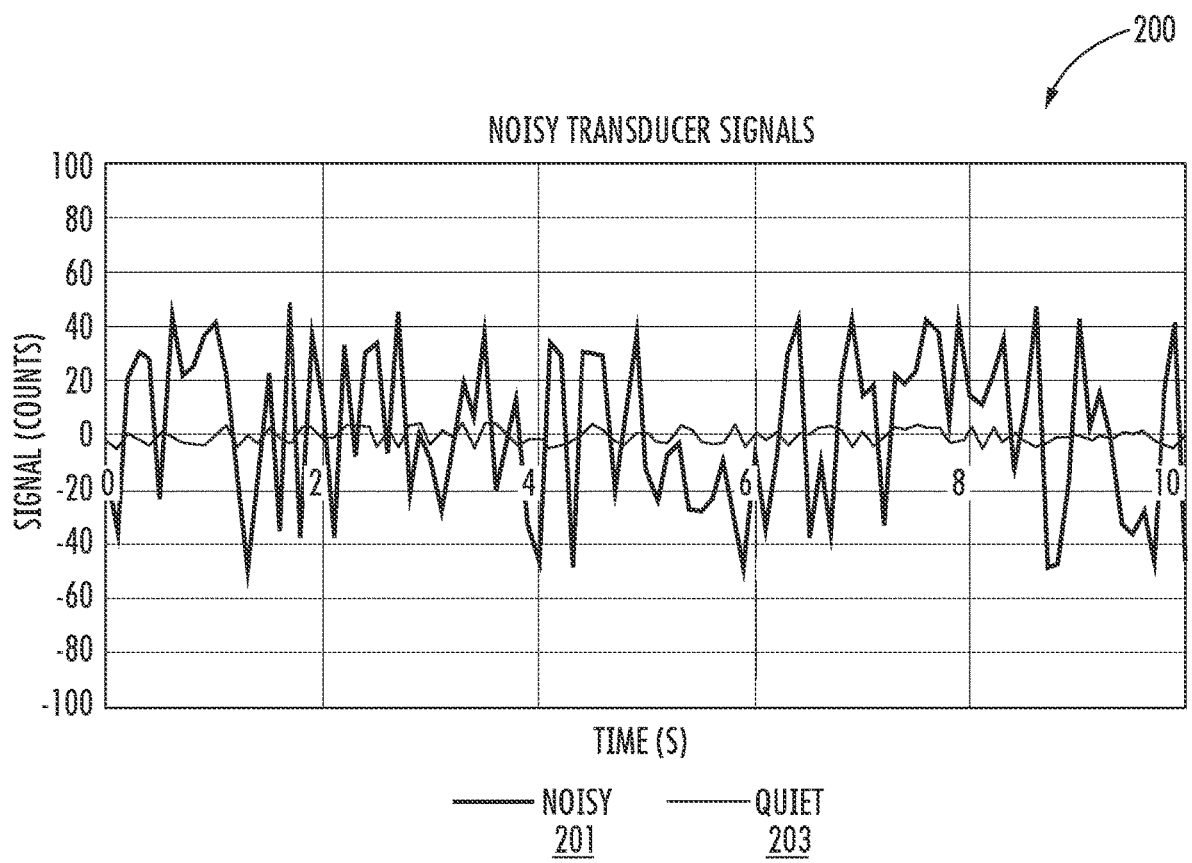
FIG. 2 illustrates a graph depicting example measurements in accordance with various embodiments of the present disclosure.

Referring now to FIG. 2, a graph 200 depicting example measurements associated with an example apparatus (e.g., a flow sensing device) in accordance with various embodiments of the present disclosure is provided.

As depicted in FIG. 2, the x-axis represents a plurality of instances in time. As depicted, the y-axis represents, for a first line 201 of the graph 200, a signal measured in counts detected by an example apparatus (e.g., a flow sensing device). As depicted, the detected signal fluctuates/varies between approximately −40 counts and +40 counts indicating that the signal is noisy. In some examples, the first line 201 of the graph may be associated with turbulent flow of a flowing media.

As depicted, the y-axis also represents, for a second line 203 of the graph, a signal measured in counts detected by an example apparatus (e.g., a flow sensing device). As depicted, the detected signal is steady and remains close to 0 counts over time indicating that the signal is quiet. In some examples, the second line 203 of the graph may be associated with laminar flow of a flowing media.

Figure 3:
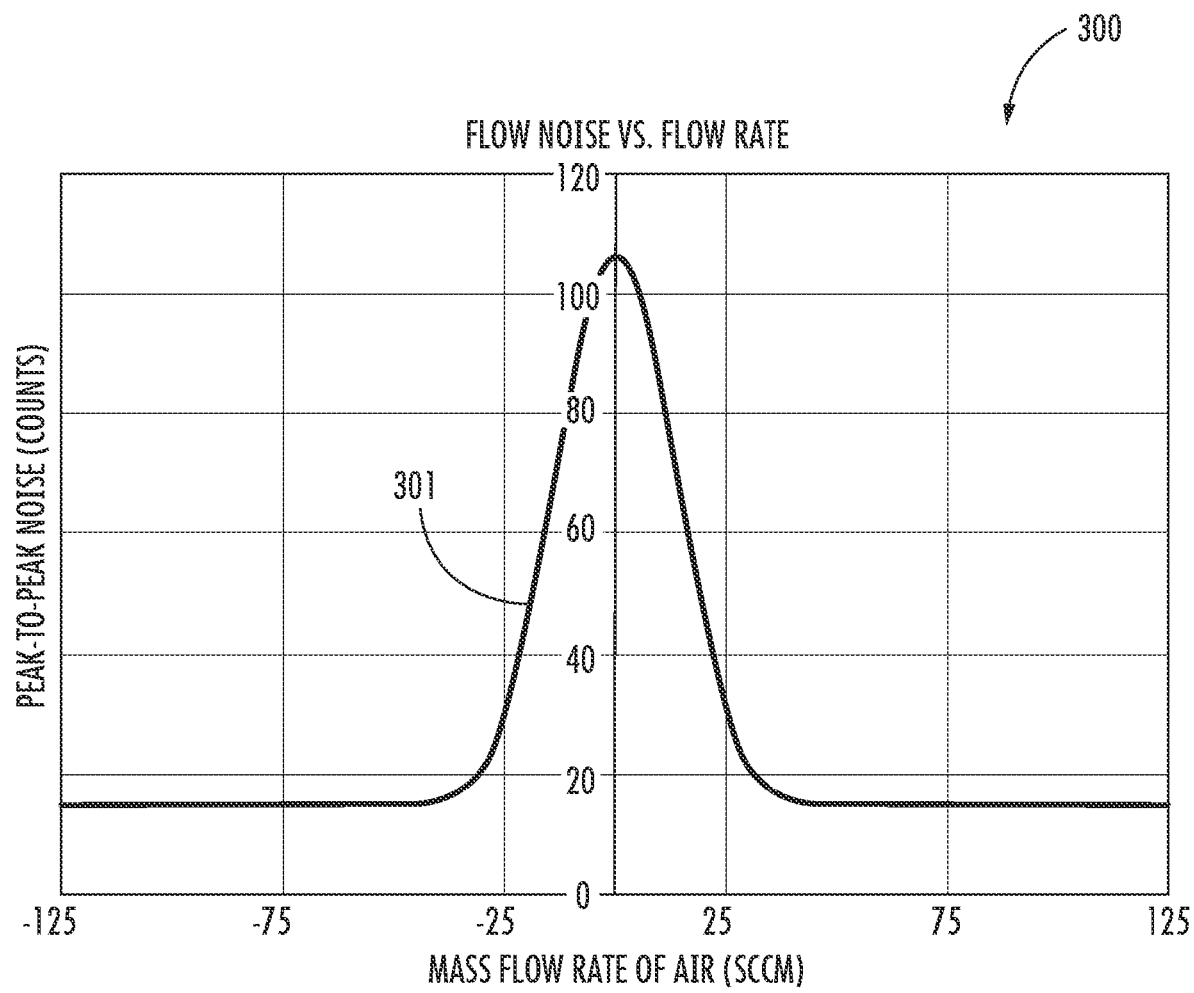
FIG. 3 illustrates a graph depicting example measurements in accordance with various embodiments of the present disclosure.

Referring now to FIG. 3, another graph 300 depicting example measurements associated with an example apparatus (e.g., a flow sensing device) in accordance with various embodiments of the present disclosure is provided.

As depicted in FIG. 3, the x-axis represents a mass flow rate of air measured in standard cubic centimeter per minute (SCCM). As further depicted, the y-axis represents, for a first line 301 of the graph 300, a signal illustrating peak-to-peak noise (measured in counts) detected by an example apparatus (e.g., a flow sensing device). As depicted, there is a minimum noise floor of approximately 15 counts when the detected mass flow rate is between −125 and −25 SCCM and +25 and +125 SCCM. As further depicted, the detected peak-to-peak noise is higher, between 20 and 105 counts when the detected mass flow rate is between −25 and 25, and peaks at 0 SCCM. Accordingly, FIG. 3 illustrates that a signal detected by an example apparatus (e.g., a flow sensing device) is noisier at/near null conditions when the flow rate of a flowing media (e.g., air) is low and peaks when there is no flow detected (as depicted, at 0 SCCM along the x-axis).

In various examples, due to physical parameters and/or innate characteristics of the flow sensing device, a signal detected by an example flow sensing device may be noisier near null conditions (e.g., in an instance in which no flow rate/air flow is detected) than at full-scale (e.g., in an instance in which higher flow rates/air flow is detected). Accordingly, the performance of a flow sensing device near null conditions is critical for optimizing device performance due to the wider tolerance at full-scale. Said differently, the noise incident in a signal detected/generated by a flow sensing device is dependent on the flow rate of a flowing media and is often the greatest at null conditions where null drift may be observed. Attempts to reduce the incidence of noise at/near null conditions (e.g., utilizing input filtering) may result in unwanted increases to the flow sensing devices response time. Additionally, compensation operations which are generally performed in order to attenuate errors during measurement have proven insufficient for reducing incident noise/null drift at null conditions. Accordingly, any technique for reducing the incidence of noise at null conditions must account for maintaining full-scale performance without degrading the response time of the flow sensing device.

To address challenges and limitations associated with measuring flow rates, various examples of the present disclosure may provide example flow sensing devices, apparatuses, methods, computer program products and systems. For example, various embodiments of the present disclosure provide digital front-end filtering techniques for turbulent flow noise removal.

In some examples, the present disclosure may provide an apparatus comprising a flow sensing component. The example flow sensing component may be configured to detect a flow rate associated with a flowing media in a flow channel of the apparatus; and a controller component in electronic communication with the flow sensing component that is configured to receive a flow rate indication from the flow sensing component, and in response to determining that the flow rate indication satisfies a null condition threshold, apply an exponential smoothing function with a variable alpha value to condition an output signal of the apparatus. In some examples, the controller component is further configured to: subsequent to applying the exponential smoothing function, perform compensation operations. In some examples, the null condition threshold is between −25 and +25 standard cubic centimeter per minute (SCCM). In some examples, the apparatus comprises a mass flow sensor or a liquid flow sensor. In some examples, the exponential smoothing function is applied to a digital front-end of the apparatus. In some examples, the controller component comprises an application-specific integrated circuit (ASIC). In some examples, a value of alpha is 1 outside the null condition threshold, and wherein the value of alpha is 0.3 at a null condition.

In various embodiments of the present disclosure, a method for filtering noise from an output signal of an apparatus is provided. The method may comprise receiving, by a controller component, a flow rate indication from a flow sensing component that is configured to detect a flow rate of a flowing media in a flow channel of the apparatus; and in response to determining, by the controller component, that the flow rate indication satisfies a null condition threshold, applying an exponential smoothing function with a variable alpha value to condition the output signal. In some examples, the method further comprises subsequent to applying the exponential smoothing function, performing, by the controller component, compensation operations. In some examples, the null condition threshold is between −25 and +25 SCCM. In some examples, the apparatus comprises a mass flow sensor or a liquid flow sensor. In some examples, the exponential smoothing function is applied to a digital front-end of the apparatus. In some examples, the controller component comprises an ASIC. In some examples, a value of alpha is 1 outside the null condition threshold, and wherein the value of alpha is 0.3 at a null condition.

In various embodiments of the present disclosure, a computer program product for filtering noise from an output signal of an apparatus is provided. The computer program product may comprise at least one non-transitory computer-readable storage medium having computer executable program code instructions therein, the computer executable program code instructions comprising program code instructions configured, upon execution, to: receive, from a flow sensing component, a flow rate indication associated with a flowing media in a flow channel of the apparatus; and in response to determining that the flow rate indication satisfies a null condition threshold, apply an exponential smoothing function with a variable alpha value to condition the output signal. In some examples, the instructions are further configured to: subsequent to applying the exponential smoothing function, perform compensation operations. In some examples, the null condition threshold is between −25 and +25 SCCM. In some examples, the apparatus comprises a mass flow sensor or a liquid flow sensor. In some examples, the exponential smoothing function is applied to a digital front-end of the apparatus. In some examples, a value of alpha is 1 outside the null condition threshold, and wherein the value of alpha is 0.3 at a null condition.

In various examples, noise may be removed from a signal detected by a flow sensing device using filtering. Filtering can be performed in a variety of places along the signal chain. In some examples, noise can be removed by filtering prior to digitization (i.e., analog filtering), at the digital front-end (i.e., filtering the raw digital transducer signal), or after digital compensation (i.e., output filter on the data). Many conventional techniques require additional external components, increasing the complexity and cost of the flow sensing device. Additionally, in some examples, these operations may degrade the response time of the flow sensing device.

By way of example, a moving average filter may be used to filter noise from a flow sensing device output signal. The example moving average filter may take N samples of input and determine the average of the N samples to produce a single output point that results in a smoother output. However, in many cases, the use of a moving average filter requires a buffer of many data points and the ability to quickly perform computations (e.g., division) which increases computational time and complexity, thereby degrading the response time of the example flow sensing device.

Using the systems, apparatuses and techniques disclosed herein, flow sensing devices configured for use in both low flow applications, high flow applications, and combinations thereof are provided. The example flow sensing devices are capable of measuring a wide range of media flow rates over several orders of magnitude with increased accuracy while reducing the incidence of noise near null conditions. As such, some examples of the present disclosure may, for example but not limited to, improve performance, sensitivity, accuracy, and/or drift of a flow sensing device. The techniques described herein include methods of digital filtering of flow sensing device/transducer signals that require no additional hardware/external components. For example, a firmware component may be added to an example flow sensing device by means of programming a filtering algorithm into the digital front-end of the signal path. In some embodiments, the novel adaptive filtering mechanism is able to adapt to varying filter parameters as a function of the flow rate. At null and very low flows, the filtering parameters are tuned high to improve null performance, and at higher flow rates, the filter parameters are tuned down as to not significantly affect the output at those flow rates.

In accordance with some embodiments of the present disclosure, an exponential smoothing function may be applied to the digital front-end to filter noise from a flow sensing device output signal. The example exponential smoothing function may take a weighted average of the current input and the previous input given by the following equation:

$$X_i = \alpha \cdot x_i + (1-\alpha) \cdot X_{i-1}$$

In the above-equation:
α is the smoothing factor;
$x_i$ is the most recent output value (not averaged);
$X_{i-1}$ is the previous averaged output; and
$X_i$ is the averaged output at current sample.

Similar to the deficiencies of the moving average filter discussed above, the exponential smoothing filter may degrade the response time depending on the value of alpha (α). For example, a low alpha value (i.e., a strong filter) may significantly degrade the response time of the example flow sensing device.

Figure 4:
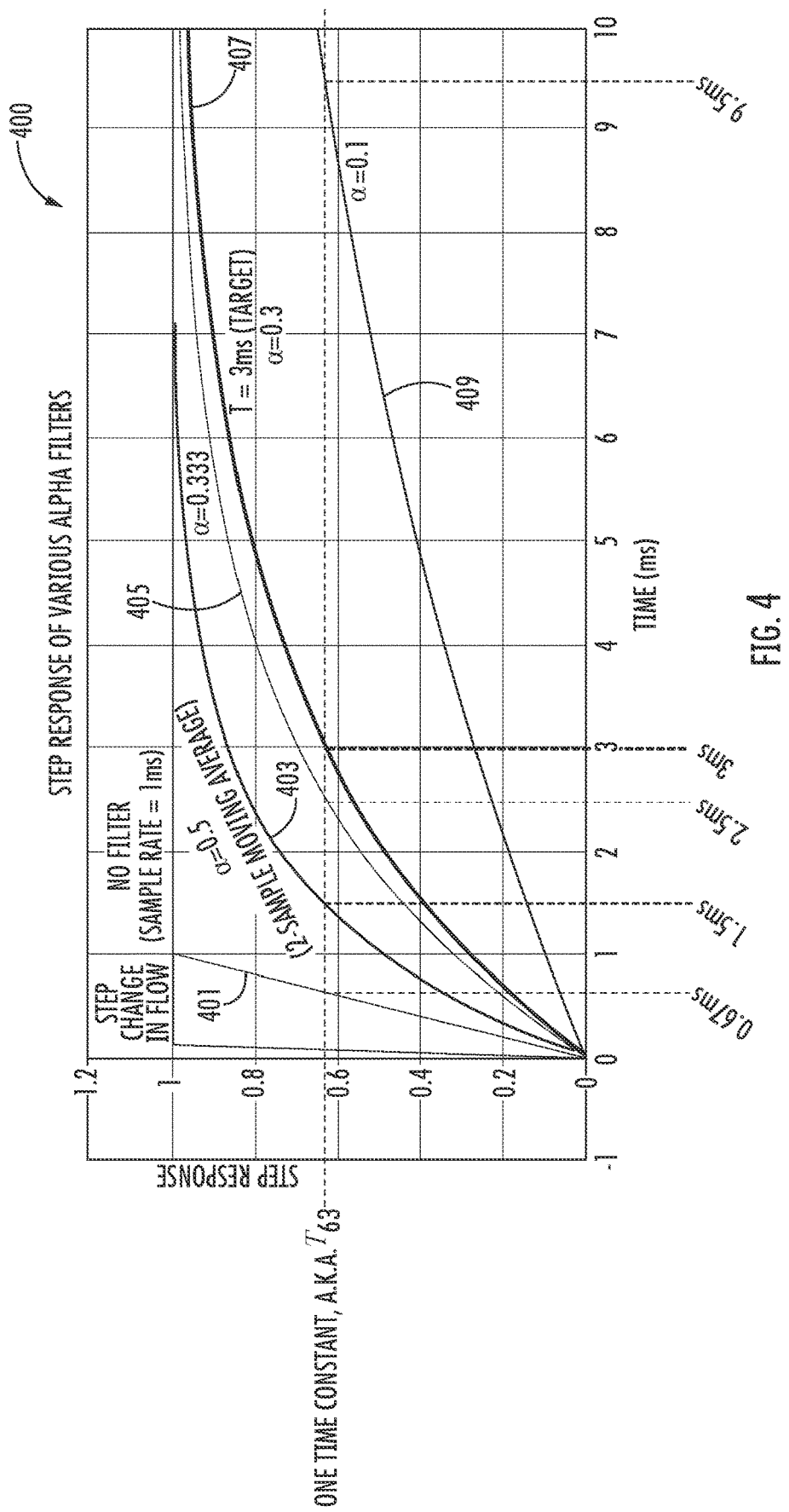
FIG. 4 illustrates a graph depicting example measurements in accordance with various embodiments of the present disclosure.

Referring now to FIG. 4, a graph 400 depicting example measurements associated with an example apparatus and various filtering configurations in accordance with various embodiments of the present disclosure is provided.

As depicted in FIG. 4, the x-axis represents a response time of an example apparatus (e.g., flow sensing device) in milliseconds (ms). As depicted, the y-axis represents, for each of a plurality of lines 401, 403, 405, 407 and 409, a detected response plot of a plurality of filtering configurations associated therewith. As further depicted in FIG. 4, a response time/responsiveness of the example apparatus (e.g., flow sensing device) may be defined as a time required for the measured output to reach 63.2% of its total step change/final value. In some embodiments, the target or optimal response time for an example apparatus (e.g., flow sensing device) may be 3 ms.

As depicted in FIG. 4, time constant value/parameter may be denoted as $T_{63}$ or, in some examples, τ. This relationship is governed by the following first order equation of a linear time-invariant (LTI) system:

$$T = (T_2 - T_1)\left(1 - \exp\left(-\frac{t}{\tau}\right)\right) + T_1$$

In the above-equation:
T is the sensor output;
$T_1$ is the initial sensor output, and $T_2$ is the currently detected sensor output such that
$(T_2-T_1)$ is the step change;
t is the time elapsed since $T_1$ was recorded; and
τ is the time constant value.

By way of example, if a sensor reading moves from 0 SCCM to 1 SCCM, the time constant, $T_{63}$, is the time required for the sensor reading to reach 63.2% of the 1 SCCM step change or 0.632 SCCM. In some examples, if the sample rate of the example apparatus is is 1 ms, then the time constant value, $$T_{63} \approx \frac{1}{\alpha}.$$

As depicted by a first line 401 of the graph 400, in an instance in which no filtering of the output of the example apparatus (e.g., flow sensing device) and the sample rate is 1 ms, the response time of the example apparatus is 0.67 ms.

As illustrated by a second line 403 of the graph 400, in an instance in which no filtering of the output of the example apparatus (e.g., flow sensing device) the response time required to reach the time constant value, $T_{63}$, is 1.5 ms.

As further depicted by a third line 405 of the graph 400, in an instance in which a moving average filter is used, and the value of alpha is 0.5, the response time required to reach the time constant value, $T_{63}$, 2.5 ms.

As further illustrated by a fourth line 407 of the graph 400, in an instance in which a moving average filter is used, and the value of alpha is 0.3, the response time required to reach the time constant value $T_{63}$, is 3 ms.

As shown by a fifth line 409 of the graph 400, in an instance in which a moving average filter is used, and the value of alpha is 0.1, the response time required to reach the time constant value $T_{63}$, is 9.5 ms.

Accordingly, FIG. 4 demonstrates that in order to satisfy a target flow response time/time constant value that is equal to or below 3 ms, the value of alpha should be greater than equal to 0.3. However, as discussed herein, the exemplary techniques of FIG. 4 are not suitable for providing accurate measurements both at/near null conditions and at full-scale.

Figure 5:
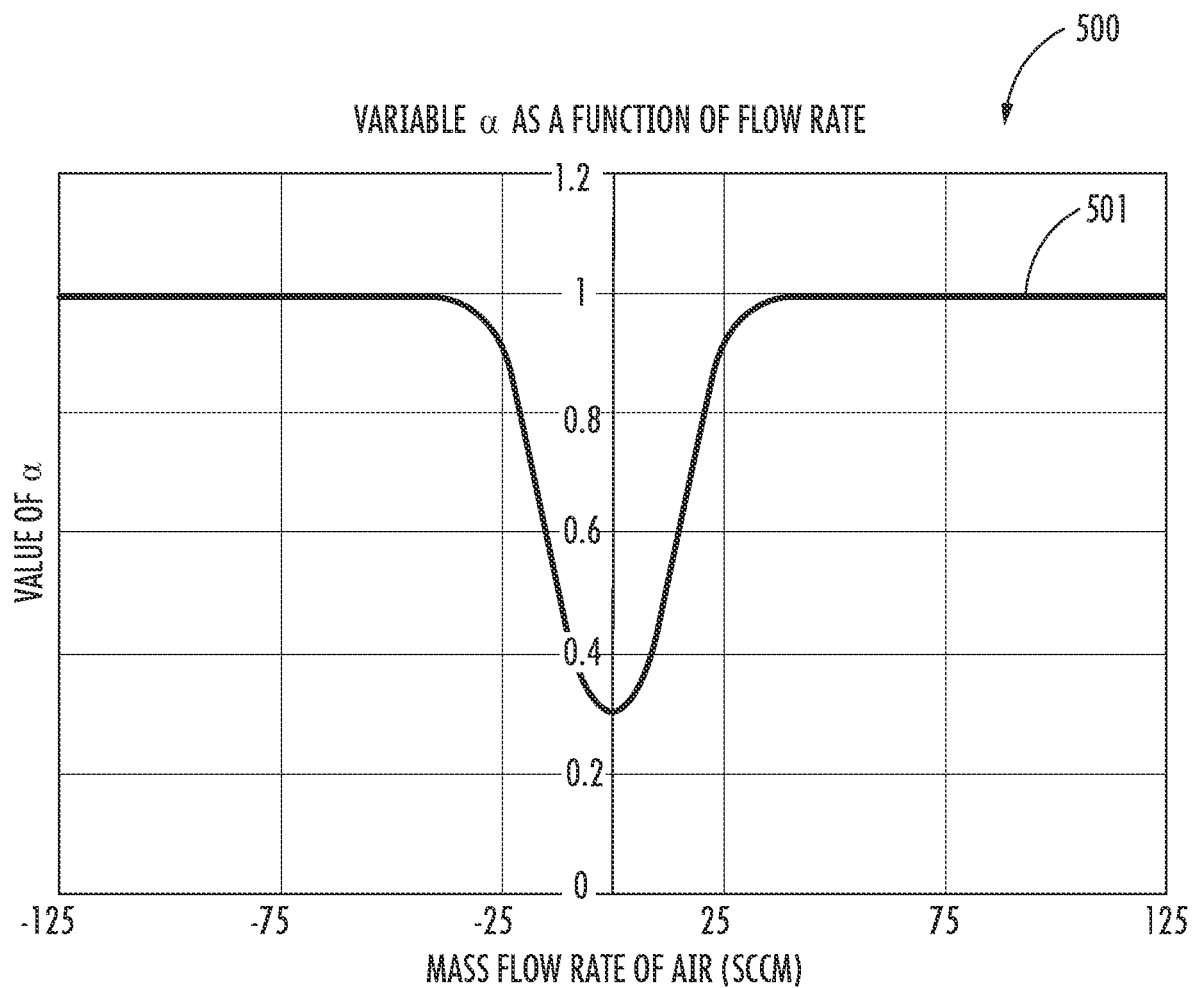
FIG. 5 illustrates a graph depicting example measurements in accordance with various embodiments of the present disclosure.

Referring now to FIG. 5, a graph 500 depicting example measurements associated with an example apparatus in accordance with various embodiments of the present disclosure is provided. The example apparatus may be configured to implement/apply an exponential smoothing function as discussed above.

As depicted in FIG. 5, the x-axis represents a mass flow rate of air measured in SCCM. As further depicted, the y-axis represents, for a first line 501 of the graph 500, an alpha value for a moving average filter utilized by an example apparatus (e.g., flow sensing device).

As depicted in FIG. 5, a value of alpha when the detected mass flow rate is approximately between −125 and −25 SCCM and +25 and +125 SCCM is 1 such that within these ranges, the full-scale performance, which requires minimal or no filtering, will be unaffected. As further depicted, the value of alpha varies when the detected mass flow rate is approximately between between −25 and +25 SCCM. For example, as shown, the value of alpha is between 0.3 and 1 when the detected mass flow rate is approximately between between −25 and +25 SCCM. Thus, in various embodiments, the example apparatus (e.g., flow sensing device) will meet the target flow response time of $T_{63} \leq 3$ ms when the value of alpha is $\geq 0.3$. Therefore, at full-scale flows, where alpha=1, no filtering operations will be performed at the flow rates (e.g., between −125 and −25 SCCM and +25 and +125 SCCM) where filtering operations are not required. Additionally, at/near null conditions, the value of alpha is equal to or close to 0.3 providing filtering operations in an instance in which they are most needed. As further depicted, between −25 SCCM and +25 SCCM, the value of alpha is an inverse function of the noise versus flow function.

Accordingly, FIG. 5 illustrates that a signal detected by an example apparatus (e.g., a flow sensing device) can be filtered using a variable alpha filter such that the example apparatus will operate optimally at/near null conditions without compromising the response of the apparatus at full-scale conditions.

Figure 6:
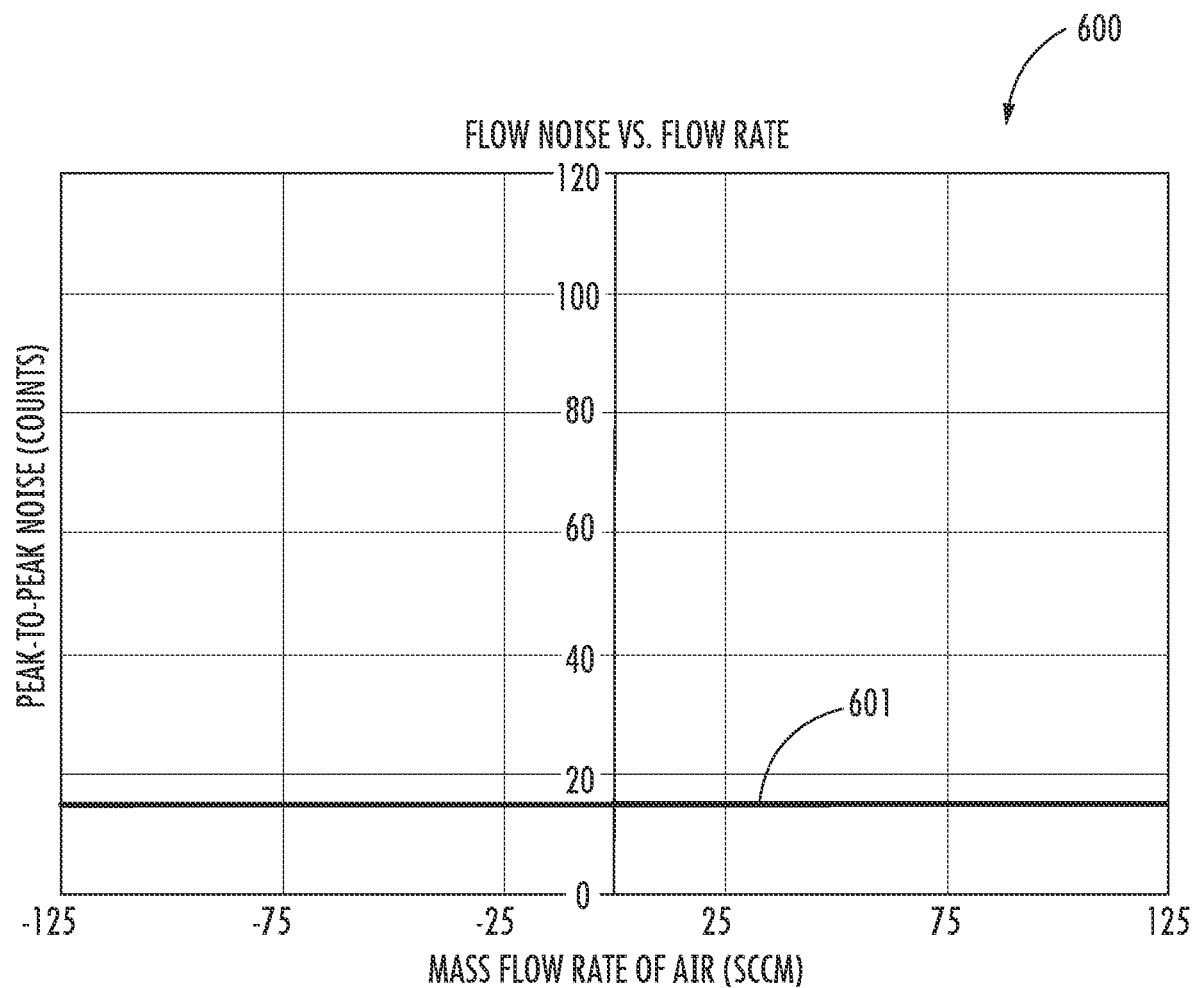
FIG. 6 illustrates a graph depicting example measurements in accordance with various embodiments of the present disclosure.

Referring now to FIG. 6, a graph 600 depicting example measurements associated with an example apparatus (e.g., a flow sensing device) in accordance with various embodiments of the present disclosure is provided. The example apparatus may implement a variable alpha filter on a digital front-end of the apparatus, such as the variable alpha filter described above in connection with FIG. 5.

As depicted in FIG. 6, the x-axis represents a mass flow rate of air measured in SCCM. As further depicted, the y-axis represents, for a first line 601 of the graph 600, a signal illustrating peak-to-peak noise (measured in counts) detected by an example apparatus (e.g., a flow sensing device). As depicted, there is a minimum noise floor of approximately 15 counts across the entirely of the operational range of the example apparatus between −125 and +125 SCCM. Accordingly, FIG. 6 illustrates that a signal detected by an example apparatus will operate optimally across its operational range to effectively filter out noise, both at/near null conditions and at full-scale conditions.

Figure 7:
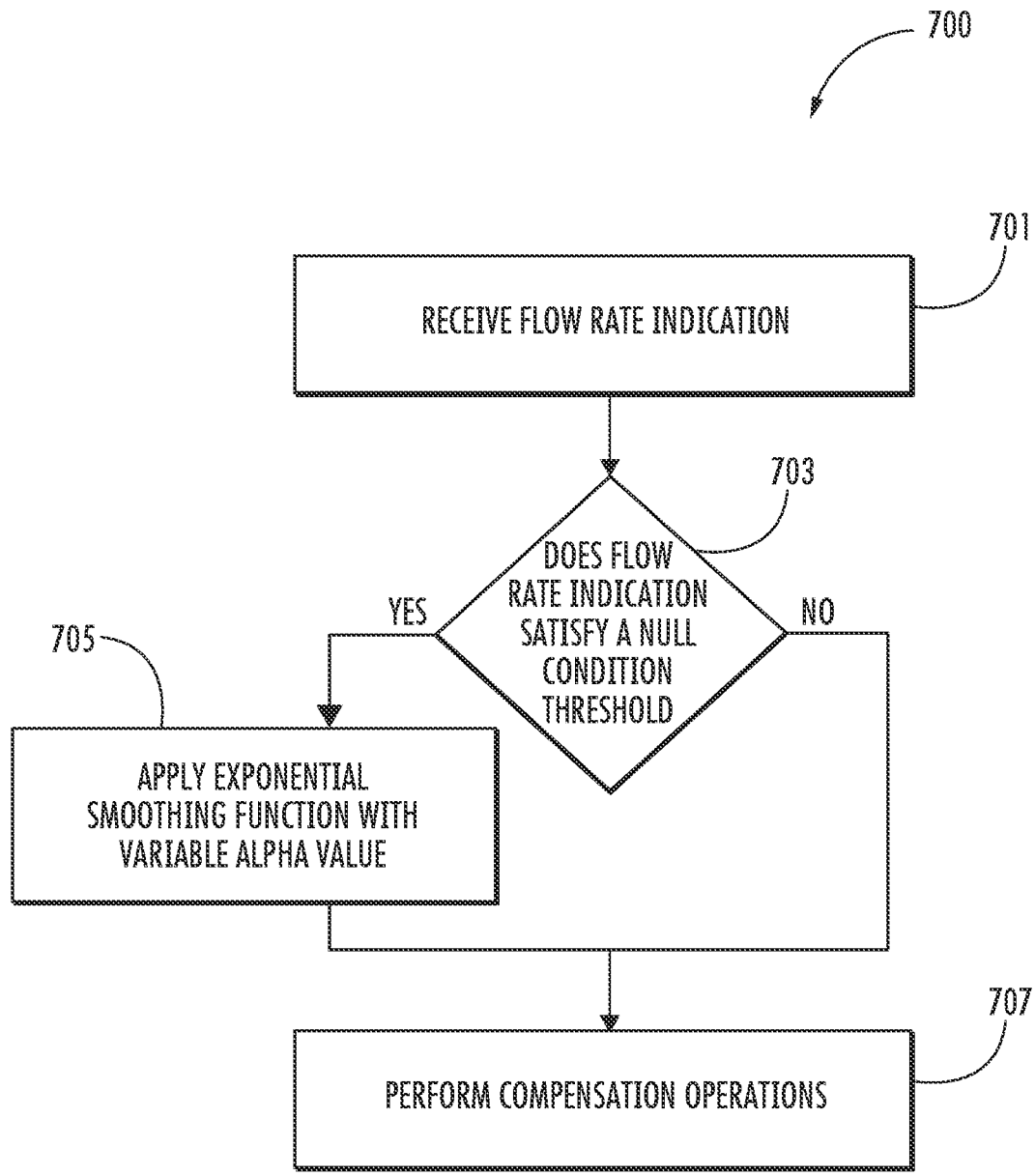
FIG. 7 is a flowchart diagram illustrating example operations in accordance with various embodiments of the present disclosure.

Referring now to FIG. 7, a flowchart diagram illustrating example operations 700 in accordance with various embodiments of the present disclosure is provided.

In some examples, the method 700 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example apparatus, such as, but not limited to, a flow sensing component, memory circuitry (such as, for example, random access memory (RAM) for storing computer program instructions), and/or a display circuitry (for rendering readings on a display).

In some examples, one or more of the procedures described in FIG. 5 may be embodied by computer program instructions, which may be stored by a memory (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram step/operation(s). Further, the system may comprise one or more other circuitries. Various circuitries of the system may be electronically coupled between and/or among each other to transmit and/or receive energy, data and/or information.

In some examples, embodiments may take the form of a computer program product on a non-transitory computer-readable storage medium storing computer-readable program instruction (e.g., computer software). Any suitable computer-readable storage medium may be utilized, including non-transitory hard disks, CD-ROMs, flash memory, optical storage devices, or magnetic storage devices.

The example method 700 begins at step/operation 701. At step/operation 701, a processing circuitry (such as, but not limited to, the processing circuitry 107 of the controller component 100 illustrated in connection with FIG. 1, discussed above) receives a flow rate indication associated with a gaseous substance (e.g., air) in a flow channel/path of an example apparatus/flow sensing device (e.g., from a flow sensing component).

Subsequent to step/operation 701, the example method 700 proceeds to step/operation 703. At step/operation 703, the processing circuitry determines whether the flow rate indication satisfies a null condition threshold. In other words, processing circuitry determines whether the detected flow rate is within a predetermined range/threshold of a null condition. In some embodiments, the null condition threshold may be a measure of an air flow rate associated with a gaseous substance in the flow channel/path that is close to or equal to zero (e.g., within a predetermined threshold of 0 SCCM). In some embodiments, an operator of the apparatus may select the null condition threshold prior to operating the apparatus.

In some embodiments, the processing circuitry may determine that the humidity level indication does not satisfy a null condition threshold if the detected air flow is equal to or within a predetermined range, for example, between −25 and +25 SCCM. In the above example, if the detected air flow is +50 SCCM, then the detected air flow does not satisfy the null condition threshold because it is outside the predetermined range of −25 and +25 SCCM. Therefore, the method 700 will proceed to step/operation 707 and the processing circuitry will proceed to perform compensation operations. In the above example, if the detected air flow is −5 SCCM, then the detected air flow satisfies the null condition threshold because it is within the predetermined range of the null condition threshold.

Subsequent to step/operation 703, and in an instance in which the detected flow rate satisfies the null condition threshold, the method 700 proceeds to step/operation 705. At step/operation 705, the processing circuitry applies an exponential smoothing function with a variable alpha value, such as the exponential smoothing function described above in relation to FIG. 5.

Subsequent to applying the exponential smoothing function at step/operation 705, at step/operation 707, the processing circuitry performs compensation operations. Thus, as discussed herein, utilizing digital front-end filtering techniques, noise can be removed from an output signal of an apparatus (e.g., flow sensing device) which preserves performance of the apparatus at full-scale while providing a strong filter at/near null conditions.

While FIG. 7 provides and example method 700, it is noted that the scope of the present disclosure is not limited to the description above. In some examples, an example process in accordance with the present disclosure may include additional and/or alternative steps/operations.

Many modifications and other embodiments of the present disclosure set forth herein will come to mind to one skilled in the art to which these embodiments pertain having the benefit of the teachings presented in the foregoing descriptions and the associated drawings. Therefore, it is to be understood that the disclosure are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. An apparatus comprising:
a flow sensing component configured to detect a flow rate associated with a flowing media in a flow channel of the apparatus; and
a controller component in electronic communication with the flow sensing component that is configured to receive a flow rate indication from the flow sensing component, and
in response to determining that the flow rate indication satisfies a null condition threshold, apply an exponential smoothing function with a variable alpha value to condition an output signal of the apparatus.

2. The apparatus of claim 1, wherein the controller component is further configured to:
subsequent to applying the exponential smoothing function, perform compensation operations.

3. The apparatus of claim 2, wherein the null condition threshold is between −25 and +25 standard cubic centimeter per minute (SCCM).

4. The apparatus of claim 1, wherein the apparatus comprises a mass flow sensor or a liquid flow sensor.

5. The apparatus of claim 1, wherein the exponential smoothing function is applied to a digital front-end of the apparatus.

6. The apparatus of claim 1, wherein the controller component comprises an application-specific integrated circuit (ASIC).

7. The apparatus of claim 1, wherein a value of alpha is 1 outside the null condition threshold, and wherein the value of alpha is 0.3 at a null condition.

8. A method for filtering noise from an output signal of an apparatus, the method comprising:
receiving, by a controller component, a flow rate indication from a flow sensing component that is configured to detect a flow rate of a flowing media in a flow channel of the apparatus; and
in response to determining, by the controller component, that the flow rate indication satisfies a null condition threshold, applying an exponential smoothing function with a variable alpha value to condition the output signal.

9. The method of claim 8, further comprising;
subsequent to applying the exponential smoothing function, performing, by the controller component, compensation operations.

10. The method of claim 9, wherein the null condition threshold is between −25 and +25 SCCM.

11. The method of claim 8, wherein the apparatus comprises a mass flow sensor or a liquid flow sensor.

12. The method of claim 8, wherein the exponential smoothing function is applied to a digital front-end of the apparatus.

13. The method of claim 8, wherein the controller component comprises an ASIC.

14. The method of claim 8, wherein a value of alpha is 1 outside the null condition threshold, and wherein the value of alpha is 0.3 at a null condition.

15. A computer program product for filtering noise from an output signal of an apparatus, the computer program product comprising at least one non-transitory computer-readable storage medium having computer executable program code instructions therein, the computer executable program code instructions comprising program code instructions configured, upon execution, to:
receive, from a flow sensing component, a flow rate indication associated with a flowing media in a flow channel of the apparatus; and
in response to determining that the flow rate indication satisfies a null condition threshold, apply an exponential smoothing function with a variable alpha value to condition the output signal.

16. The computer program product of claim 15, wherein the instructions are further configured to:
subsequent to applying the exponential smoothing function, perform compensation operations.

17. The computer program product of claim 16, wherein the null condition threshold is between −25 and +25 SCCM.

18. The computer program product of claim 15, wherein the apparatus comprises a mass flow sensor or a liquid flow sensor.

19. The computer program product of claim 15, wherein the exponential smoothing function is applied to a digital front-end of the apparatus.

20. The computer program product of claim 15, wherein a value of alpha is 1 outside the null condition threshold, and wherein the value of alpha is 0.3 at a null condition.

\* \* \* \* \*